(12) United States Patent
Marquez-Flores

(10) Patent No.: US 11,980,683 B2
(45) Date of Patent: May 14, 2024

(54) HAIR CARE OIL COMPOSITION AND METHOD OF USE

(71) Applicant: Locks of Liz Haircare LLC, Willimantic, CT (US)

(72) Inventor: Lizbeth Marquez-Flores, Windham, CT (US)

(73) Assignee: Locks of Liz Haircare LLC, Willimantic, CT (US)

( * ) Notice: Subject to any disclaimer, the term of this patent is extended or adjusted under 35 U.S.C. 154(b) by 119 days.

(21) Appl. No.: 17/719,587

(22) Filed: Apr. 13, 2022

(65) Prior Publication Data

US 2022/0331232 A1  Oct. 20, 2022

Related U.S. Application Data

(60) Provisional application No. 63/175,531, filed on Apr. 15, 2021, provisional application No. 63/175,533, filed on Apr. 15, 2021.

(51) Int. Cl.
| | |
|---|---|
| *A61Q 5/06* | (2006.01) |
| *A61K 8/06* | (2006.01) |
| *A61K 8/92* | (2006.01) |
| *A61K 8/9789* | (2017.01) |
| *A61Q 5/12* | (2006.01) |

(52) U.S. Cl.
CPC ............ *A61K 8/9789* (2017.08); *A61K 8/062* (2013.01); *A61K 8/922* (2013.01); *A61Q 5/06* (2013.01); *A61Q 5/12* (2013.01); *A61K 2800/31* (2013.01); *A61K 2800/5922* (2013.01); *A61K 2800/88* (2013.01)

(58) Field of Classification Search
None
See application file for complete search history.

(56) References Cited

U.S. PATENT DOCUMENTS

| | | | |
|---|---|---|---|
| 6,312,675 B1 * | 11/2001 | Deane | A61K 8/645 424/735 |
| 2010/0092582 A1 * | 4/2010 | Anderson | A61K 36/00 424/727 |

OTHER PUBLICATIONS

R K Roy et al., Hair growth promoting activity of Eclipta alba in male albino rats, Arch Dermatol Res. Aug. 2008;300(7):357-64. doi: 10.1007/s00403-008-0860-3. Epub May 14, 2008.

S. Begum, et al., Exogenous stimulation with Eclipta alba promotes hair matrix keratinocyte proliferation and downregulates TGF-81 expression in nude mice, International Journal of Molecular Medicine, pp. 496-502, 2014, Published online on: Dec. 4, 2014 doi.org 10.3892 ijmm 2014.2022.

* cited by examiner

*Primary Examiner* — Brian Gulledge
(74) *Attorney, Agent, or Firm* — Wiggin and Dana LLP

(57) ABSTRACT

A hair care oil composition including *Eclipta alba*. The compositions are useful for treating the hair and scalp.

12 Claims, 6 Drawing Sheets

Panel A                    Panel B

Panel A                    Panel B

Panel A / Panel B

Panel A            Panel B

Panel A  Panel B

Panel A          Panel B

HAIR CARE OIL COMPOSITION AND METHOD OF USE

CROSS-REFERENCE TO RELATED APPLICATIONS

This application claims the benefit under 35 U.S.C. § 119(e) of U.S. Provisional Application No. 63/175,531 filed Apr. 15, 2021, and U.S. Provisional Application No. 63/175,533 filed Apr. 15, 2021, all of which are herein incorporated by reference in their entirety.

FIELD OF THE INVENTION

A hair care oil composition including *Eclipta alba*. The compositions are useful for treating the hair and scalp, and in particular for wavy, curly, or coily/kinky hair.

BACKGROUND OF THE INVENTION

Although there are a myriad of hair care products, many of them contain petroleum-derived and other highly manufactured ingredients. It is not uncommon for hair care products to contain non-natural and potentially irritating, allergenic, antigenic, or toxic components.

Furthermore, there is an increasing trend in consumer preferences for selecting natural and environmentally friendly products. According to publicly available information, the entire global hair care product market in 2019 was estimated at over $170 billion. The global market for natural hair care products has been growing and in 2019 was estimated at nearly $9 billion, with this trend expected to continue.

The awareness of the benefits of natural hair care products is one of the factors contributing to this market growth. With the preference by an increasing number of consumers for natural and environmentally friendly products, many of the more conventional products are seen as less desirable. There are many reasons for this preference towards natural products including environmental awareness and the avoidance of highly manufactured and refined products or products with artificial ingredients. Some consumers perceive detrimental effects with using more mainstream hair care products such as product harshness, scalp irritation, and poor hair quality such as dryness, split ends, and loss of sheen. Furthermore, individuals with product allergies or compromised immune systems, such as individuals undergoing chemotherapy, may not be able to use many of the mainstream commercial products. Consumers are also becoming more informed and savvier about product ingredients. These consumers carefully read product labels and avoid selecting products with ingredients such as sulfates, parabens, para-aminobenzoic acid, ethyl alcohol, mineral oil, and various additives and artificial ingredients.

Another area where there has been a need for innovative and natural hair care products is for wavy, curly, or coily hair, and in particular for the ethnic hair care market. There is a general relationship between ethnicity and hair types with Caucasian hair being the finest in diameter with the highest scalp density and variations in straightness or curliness, Asian hair being the coarsest in diameter with a medium scalp density and hair being the straightest, and African/Australoid hair being of variable diameter with the lowest scalp density and also generally of the curliest form. Based on these general hair type characteristics, there is consumer demand for natural hair care products that are particularly useful for treating and styling wavy, curly, or coily hair types.

Based on these trends and needs, consumers are also becoming increasingly aware of natural ingredients, such as plant-based ingredients or botanicals, and their suitability for a wide array of hair care products. Consequently, there is an increased interest in and demand for hair care products formulated with natural ingredients, and particularly for products designed for use with wavy, curly, or coily hair.

Not only women, but also male consumers are becoming increasingly aware of and using hair care products for their hair and beards. Many of these male consumers are also looking for naturally formulated products without petroleum-based and artificial ingredients.

It has been found in the present invention that hair care oil compositions containing *Eclipta alba* have highly desirable properties for treating the hair and scalp, for example, curly hair. The present invention therefore overcomes the challenges of providing naturally based compositions and methods for treating hair.

SUMMARY OF THE INVENTION

A hair care composition including *Eclipta alba*. The compositions are useful for treating the hair and scalp, and in particular wavy, curly, or coily hair.

In some embodiments the present invention provides an oil composition for treating hair comprising *Eclipta alba*.

In other embodiments the present invention provides a composition for treating hair consisting of *Eclipta alba*, sweet almond oil, sesame seed oil, argan oil, castor oil, rosemary essential oil, grapefruit essential oil, and peppermint essential oil.

In other embodiments the present invention provides a composition for treating hair comprising *Eclipta alba*, sweet almond oil, sesame seed oil, argan oil, castor oil, rosemary essential oil, grapefruit essential oil, and peppermint essential oil.

In other embodiments the present invention provides a composition for treating hair comprising (i) from about 3.5% to about 4.0% *Eclipta alba*, (ii) from about 90% to about 95% of an oil (a "first oil") selected from the group consisting of sesame seed oil, coconut oil, grape seed oil, sweet almond oil, castor oil, Jamaica black castor oil, argan oil, and mixtures thereof, and (iii) from about 0.5% to about 1.5% of an essential oil selected from the group consisting of rosemary essential oil, grapefruit essential oil, peppermint essential oil, and mixtures thereof.

Note that the oil "(ii)" can also be referred to as the "first oil" component so that it is distinguished from and not confused with the essential oil component "(iii)". Although both the first oil component (ii) and the essential oil (iii) are broken out and described separately for the sake of convenience and to describe the invention, these oils can together form part of the oil phase of the compositions herein.

In other embodiments the present invention provides a composition that is substantially free of water.

In other embodiments the present invention provides a composition comprising less than about 5% by weight water.

In other embodiments the present invention provides a composition for treating hair comprising (i) *Eclipta alba*, (ii) an oil (a "first oil") selected from the group consisting of sesame seed oil, coconut oil, grape seed oil, sweet almond oil, castor oil, Jamaica black castor oil, argan oil, and mixtures thereof, and (iii) an essential oil selected from the group consisting of rosemary essential oil, grapefruit essential oil, peppermint essential oil, and mixtures thereof.

In other embodiments the present invention provides a composition wherein the *Eclipta alba* comprises from about 0.1% to about 20% by weight of the composition, or from about 0.5% to about 10% by weight, or from about 1% to about 5% by weight, or from about 2% to about 4.5% by weight, or from about 3% to about 4.25% by weight, or from about 3.5% to about 4.2% by weight, or from about 3.5% to about 4.0% by weight, or from about 3.6% to about 4.1% by weight, or from about 3.7% to about 4.0% by weight, or about 2.5% by weight, or about 3.0% by weight, or about 3.5% by weight, or about 4% by weight of the composition.

In other embodiments the present invention provides a composition wherein the oil [i.e., the oil (ii) or first oil component] comprises from about 80% to about 99% by weight, or from about 85% to about 98% by weight, or from about 88% to about 96% by weight, or from about 90% to about 95% by weight, or about 90% by weight, or about 91% by weight, or about 92% by weight, or about 93% by weight, or about 94% by weight, or about 95% by weight of the composition.

In other embodiments the present invention provides a composition wherein the essential oil (iii) comprises from about 0.1% to about 2.5% by weight, or about 0.2% to about 2.0% by weight, or about 0.5% to about 1.5% by weight, or about 0.8% to about 1.2% by weight, or about 1% by weight, or about 1.1% by weight, or about 1.2% by weight of the composition.

In other embodiments the present invention provides a composition wherein the hair is human hair.

In other embodiments the present invention provides a composition wherein the human hair is wavy (Type 2 hair), curly (Type 3 hair), or coily/kinky (Type 4 hair) human hair, or the hair is selected from any hair type.

In other embodiments the present invention provides a kit for treating human hair comprising a composition of the present invention and instructions for using.

In other embodiments the present invention provides a kit further comprising a companion cream product for treating hair.

In other embodiments the present invention provides a method for treating human scalp hair comprising applying an effective amount of a composition according to the present invention to human scalp hair.

In other embodiments the present invention provides a method for styling human scalp hair comprising applying an effective amount of a composition according to the present invention to human scalp hair.

In other embodiments the present invention provides a method for conditioning human scalp hair comprising applying an effective amount of a composition according to the present invention to human scalp hair.

In other embodiments the present invention provides a method for treating human beard hair comprising applying an effective amount of a composition according to the present invention to human beard hair.

In other embodiments the present invention provides a method for treating or massaging the scalp of a human comprising applying or massaging an effective amount of a composition according to the present invention to the scalp.

In other embodiments the present invention provides a method for making a composition for treating hair comprising the step of combining *Eclipta alba*, sweet almond oil, sesame seed oil, argan oil, castor oil, rosemary essential oil, grapefruit essential oil, and peppermint essential oil. The combining of the ingredients can be facilitated by mixing, stirring, or shaking.

In other embodiments the present invention provides a composition wherein the oil phase is of low viscosity, such that at ambient room temperature, i.e. about 25° C., the viscosity is from about 10 mPas to about 1000 mPas, or from about 50 mPas to about 200 m Pas.

In other embodiments the present invention provides a composition further comprising an antimicrobial agent and/or an anti-oxidant.

In other embodiments the present invention provides a composition wherein the antimicrobial agent and/or the anti-oxidant is selected from the group consisting of rosemary essential oil, grapefruit essential oil, and mixtures thereof.

In other embodiments the present invention provides a composition further comprising a fragrance.

In other embodiments the present invention provides a composition wherein the fragrance is selected from peppermint oil essential oil.

In other embodiments the present invention provides a product for treating hair comprising a composition according to the present invention and further comprising a container or applicator.

These and other embodiments of the present invention will become apparent from the disclosure herein.

DETAILED DESCRIPTION OF THE INVENTION

Definitions

Figure 1:
FIG. 1 shows before and after photos of the hair of a female subject treated with one application of both an oil and a cream product. The panel on the left (panel A) shows the hair before treatment and the panel on the right (panel B) shows the hair after treatment).
Figure 2:
FIG. 2 shows before and after photos of the hair of a female subject treated over a period of 8 months with an oil product and a cream product. The oil product was used occasionally. The panel on the left (panel A) shows the hair before treatment and the panel on the right (panel B) shows the hair after treatment for 8 months.
Figure 2:
Figure 3:
FIG. 3 shows before and after photos of the hair of a male subject treated over a period of 1 month with an oil product The panel on the upper left (panel A) shows the hair before treatment and the panel on the lower right (panel B) shows the hair after treatment for 1 month.
Figure 4:
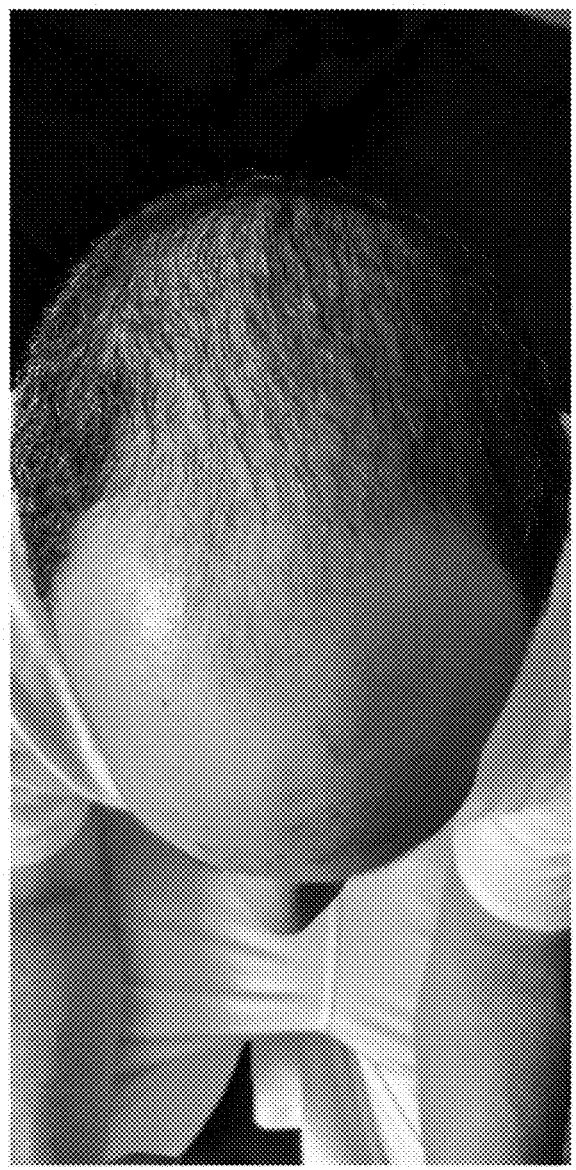
FIG. 4 shows before and after photos of the hair of a male subject treated over a period of 2.5 months with an oil product The panel on the left (panel A) shows the hair before treatment and the panel on the right (panel B) shows the hair after treatment for 2.5 months.
Figure 4:
Figure 5:
FIG. 5 shows before and after photos of the hair of a female subject treated over a period of 4 months with a cream product. The panel on the left (panel A) shows the hair before treatment and the panel on the right (panel B) shows the hair after treatment for 4 months.
Figure 6:
FIG. 6 shows before and after photos of the hair of a male subject treated over a period of 1 week with three treatments of an oil product. The panel on the left (panel A) shows the hair before treatment and the panel on the right (panel B) shows the hair after treatment for 1 week.

As used herein, the following terms and abbreviations have the indicated meanings unless expressly stated to the contrary.

The term "cosmetically acceptable", as used herein means that the compositions are suitable for applying to the hair or skin for providing cosmetic benefits.

The term "CTFA", as used herein means Cosmetic, Toiletry & Fragrance Association.

The abbreviations "e.o." and "E.O." as used herein means "essential oil".

The term "substantially free of water" means that the compositions contain less than about 10% by weight water, or less than about 5% by weight water, or less than about 2.5% by weight water, or less than about 2% by weight water, or less than about 1.5% by weight water, or less than about 1% by weight water, or less than about 0.5% by weight water, or less than about 0.25% by weight water, or less than about 0.1% by weight water. The water content can ideally be 0% by weight water or as practically close to 0% such that no appreciable amount of water is intended to be added or incorporated into the compositions, such that the composition is substantially free of water.

The terms "treat," "treating" or "treatment," as used herein, include alleviating, abating or ameliorating the condition.

Hair Care Oil Composition

The present invention provides natural hair and scalp care compositions, tools, and accessories which restore and maintain natural waves, curls, coils, and kinks. The present invention aims to ease daily hair care routines and increases the confidence of the users to shine bright from the inside out.

Part of the impetus for the present invention was based on wanting to help others, giving hair advice to patients, friends, and anyone who would listen. One fateful day, after realizing the desperation of a cancer patient with the loss of her hair, the inventor gave the patient advice on her hair loss journey and how the inventor could help her get through it. The inventor realized how important hair really is to a person, especially women. The inventor decided to create a business that would provide people unique tools and products to embrace their natural locks, grow long, healthy curls with manageability, and boost their confidence in the process.

The inventor's background experience as a medical professional in cancer care provided a basis from which to understand the ravaging effect that chemicals can have on a person's hair, and, as a result, their self-esteem. Therefore, the inventor chose to research natural ingredients from around the world, which led to many plant extracts and essential oils that have been proven to aid in the hair concerns and conditions that affect those with curls. Unfortunately, these ingredients have not been readily utilized in the natural hair products that are currently on the market until now.

The compositions described herein are oil compositions. These compositions generally have a single oil phase and do not contain any appreciable amounts of water or an aqueous phase.

Curl Type Classification

As described above, there is a general relationship between ethnicity and hair types with Caucasian hair being the finest in diameter with the highest scalp density and variations in straightness or curliness, Asian hair being the coarsest in diameter with a medium scalp density and hair being the straightest, and African/Australoid hair being of variable diameter with the lowest scalp density and also generally of the curliest form.

Hair can be described into what are now considered professionally recognized types. These types are based on four general types and three subtypes or subclassifications. The four general hair types are:

Type 1 is straight
Type 2 is wavy
Type 3 is curly, and
Type 4 is coily/kinky.

The three hair subtypes are based on the width or diameter of the wave, curl, or coil pattern. The three hair subtypes are:

Subtype A is a wide pattern size
Subtype B is a medium pattern size,
Subtype C is a small pattern size.

For example, hair that is wavy with a medium pattern size would be classified as Type 2B. Another example would be hair that is curly with a medium pattern size, which would be classified as Type 3B.

Although the compositions of the present invention can be used on any hair type, the compositions of the present invention are particularly useful for hair of curly and coily types with medium and small curl and coli patterns, such as Types 3B, 3C, 4B, and 4C, i.e., types 3B to 4C.

*Eclipta alba*

The present invention utilizes *Eclipta alba*. *Eclipta alba* (L.) Hassk. Is also known as *Eclipta prostrata* Roxb. and belongs to the Asteraceae family and is commonly known as false daisy in English and bhringoraj or bhringraj in Bangladesh and India. The plant is a species in the sunflower family and widely distributed in warm temperate to tropical areas and found in particular in India, Nepal, China, Thailand, and Brazil. The plant has cylindrical grayish roots and solitary flower heads with white florets. The plant is believed to contain various phytochemicals, such as coumestans, polypeptides, polyacetylenes, thiophene derivatives, steroids, sterols, triterpenes, and flavonoids. The whole dried plant has been used in traditional medicine.

The following references describe *Eclipta alba*:

R K Roy et al., Hair growth promoting activity of *Eclipta alba* in male albino rats, Arch Dermatol Res. 2008 August; 300(7):357-64. doi: 10.1007/s00403-008-0860-3. Epub 2008 May 14.

S. Begum, et al., Exogenous stimulation with *Eclipta alba* promotes hair matrix keratinocyte proliferation and downregulates TGF-β1 expression in nude mice, International Journal of Molecular Medicine, pages 496-502, 2014, Published online on: Dec. 4, 2014 doi.org 10.3892 ijmm 2014.2022.

Various forms of *Eclipta alba* can be used in the present invention, including oils, essential oil forms, extracts, and solid forms such as the dried whole plant which can be ground or pulverized into a powder.

The compositions of the present invention can comprise a wide range of *Eclipta alba*. Some exemplary ranges comprise from about 0.1% to about 20% by weight of the composition, or from about 0.5% to about 10% by weight, or from about 1% to about 5% by weight, or from about 2% to about 4.5% by weight, or from about 3% to about 4.25% by weight, or from about 3.5% to about 4.2% by weight, or from about 3.5% to about 4.0% by weight, or from about 3.6% to about 4.1% by weight, or from about 3.7% to about 4.0% by weight, or about 2.5% by weight, or about 3.0% by weight, or about 3.5% by weight, or about 4% by weight of the composition.

Oil Phase

The compositions of the present invention comprise an oil phase. Typically, the oil phase comprises a combination of oil materials. Examples of oil phase materials can comprise those selected from the group consisting of sesame seed oil, coconut oil, grape seed oil, sweet almond oil, castor oil, Jamaican black castor oil, argan oil, and combinations thereof. These oils can be referred to as "oil component (ii)" or a "first oil".

The oil phase can also contain other oils such as essential oils (iii) as described here and in other sections of this application. The essential oil can be selected from the group consisting of, such as, rosemary essential oil, grapefruit essential oil, peppermint essential oil, and mixtures thereof. The essential oils can be referred to as "essential oils (iii)."

As described above, note that the oil "(ii)" can also be referred to as the first oil component so that it is distinguished from and not confused with the essential oil component "(iii)". Although both the first oil component (ii) and the essential oil (iii) are broken out and described separately for the sake of convenience and to describe the invention, these oils can together form part of the oil phase of the compositions herein.

As described above, the present invention provides a composition wherein the oil [i.e., the oil (ii) or first oil component] comprises from about 80% to about 99% by weight, or from about 85% to about 98% by weight, or from about 88% to about 96% by weight, or from about 90% to about 95% by weight, or about 90% by weight, or about 91% by weight, or about 92% by weight, or about 93% by weight, or about 94% by weight, or about 95% by weight of the composition.

As also described above, the present invention provides a composition wherein the essential oil (iii) comprises from about 0.1% to about 2.5% by weight, or about 0.2% to about 2.0% by weight, or about 0.5% to about 1.5% by weight, or about 0.8% to about 1.2% by weight, or about 1% by weight, or about 1.1% by weight, or about 1.2% by weight of the composition.

As discussed above, the present invention provides a composition wherein the oil phase is of low viscosity, such that at ambient room temperature, i.e. about 25° C., the viscosity is from about 10 mPas to about 1000 mPas, or from about 50 mPas to about 200 m Pas.

Other Components

The compositions can comprise other components, which are preferably derived from naturally derived sources, such as plant sources.

The compositions can also comprise an antimicrobial agent and/or an anti-oxidant. The antimicrobial agent and/or the anti-oxidant can be selected from the group consisting of rosemary e.o., grapefruit e.o., and mixtures thereof.

The compositions can also comprise a fragrance. The fragrance can be selected from the group consisting of peppermint oil (essential oil).

Note that even though these essential oils are described here for convenience, they are intended as being defined as essential oils that are part of the essential oil component (iii) of the invention.

Preparation Methods

The compositions can be made using standard formulation and mixing techniques familiar to one of ordinary skill in the art of pharmaceuticals and formulations.

One of ordinary skill in the pharmaceutical and formulation arts can determine the appropriate levels of the essential and optional components of the compositions of the present invention.

Packaging and Kits

The compositions can be packaged and dispense from jars, bottles, and other containers. The compositions can be packaged as kits with other products and would generally contain labeling and instructions for use.

Methods of Use and Treating Hair and Skin

The present invention utilizes a cosmetically effective amount of the compositions for treating hair and the scalp (the skin on the head), as well as treating beard hair. The compositions are typically applied to the hair and scalp or to the beard. The compositions can be gently massaged into the scalp. The compositions can also be worked into the hair from the root end to the hair end. The products are generally leave-on products but can also be washed out.

Various treatment regimens can be prescribed and used based on the preference of the consumer or practitioner. In some embodiments, the compositions can be applied at least once daily. In other embodiments, composition can be applied least twice weekly or at least once weekly. The products can be used until the desired hair and scalp benefits are obtained.

Additionally, the oil product is useful for protecting hair from heat damage, such as when one straightens hair with an iron or other such device. For this use the hair is pre-treated with the oil prior to straightening with the heating device. Furthermore, most of the oils [particularly the (ii) oils which can also be referred to as the first oil component] used in the product can be selected to have a high smoke point to withstand the heat of the heating device. Examples of some smoke points are the following: almond oil—430° F., argan oil—420° F., castor oil—395° F., and sesame seed oil—410° F.

Evaluation of Treatments

The performance of the products can be evaluated by various means, including self-assessment by the user such as visually and tactically. The performance of the products can also be evaluated by the judgement of third parties. The performance of the products can also be evaluated instrumentally by various objective measures such as breaking strength using for example an Instron brand measuring device, curl strength, and roughness.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Example 1: Lock Length Oil Formula

The following composition is prepared using standard mixing equipment and procedures. Note that the ingredients are provided on a weight percentage, i.e. (w/w) % for this example.

| Ingredient | Amount | (Weight Percent) |
| --- | --- | --- |
| Sweet Almond Oil | 40.81 grams | 35.42% |
| Sesame Seed Oil | 40.81 | 35.42 |

-continued

| Ingredient | Amount | (Weight Percent) |
| --- | --- | --- |
| Castor Oil | 14.33 | 12.44 |
| Argan Oil | 13.46 | 11.68 |
| *Eclipta alba*\* | 4.53 | 3.93 |
| Rosemary essential oil | 0.32 | 0.28 |
| Grapefruit essential oil | 0.46 | 0.40 |
| Peppermint essential oil | 0.50 | 0.43 |

\*An oil form or a powdered form can be used.

The carrier oils, i.e. the sweet almond oil, sesame seed oil, castor oil, and argan oil, are added via a funnel into a container that can be capped. Next the *Eclipta alba* is added, followed by adding the rosemary, grapefruit, and peppermint essential oils by a dropper. The container is capped and shaken well to mix the ingredients.

The composition can be packaged in an ordinary bottle or dispensing bottle.

The composition is useful for treating the scalp and hair and in particular for curl types 3B to 4C.

For use for scalp care, the product is massaged into scalp two to three times a week. Depending on hair type, the user can leave the product on. For example, users with non-curly hair types may prefer to leave the product on for half an hour or over night before washing out.

For moisturizing the hair, the product is evenly applied through the length of the hair. The product can also be applied to beards for added softness.

The product can be used as a base in combination with the curl lock creams of Examples 5 to 8, below.

The composition can provide cosmetic benefits to the scalp and hair and to enhance the appearance of the hair and its feel of thickness and to reduce frizz and split ends.

Example 2: Lock Length Oil Formula

The following composition is prepared using standard mixing equipment and procedures.

| Ingredient | Amount |
| --- | --- |
| Sweet Almond Oil | 1.5 oz. |
| Sesame Seed Oil | 1.5 oz. |
| Castor Oil | 1 oz. |
| *Eclipta alba* | 1 tsp |
| Rosemary essential oil | 12 drops |
| Grapefruit essential oil | 14 drops |
| Peppermin essential oil | 20 drops |

The carrier oils, i.e. the sweet almond oil, sesame seed oil, and castor oil are added via a funnel into a container that can be capped. Next the *Eclipta alba* is added, followed by adding the rosemary, grapefruit, and peppermint essential oils by a dropper. The container is capped and shaken well to mix ingredients.

The composition can be packaged in an ordinary bottle or dispensing bottle.

The composition is useful for treating the scalp and hair and in particular for curl types 3B to 4C.

For use for scalp care, the product is massaged into scalp two to three times a week. Depending on hair type, the user can leave the product on. For example, users with non-curly hair types may prefer to leave the product on for half an hour or over night before washing out.

For moisturizing the hair, the product is evenly applied through the length of the hair. The product can also be applied to beards for added softness.

The product can be used as a base in combination with the curl lock creams of Examples 5 to 8, below.

The composition can provide cosmetic benefits to the scalp and hair and to enhance the appearance of the hair and its feel of thickness and to reduce frizz and split ends.

Example 3: Lock Length Oil Formula

The following composition is prepared using standard mixing equipment and procedures.

| Ingredient | Amount |
| --- | --- |
| Sweet Almond Oil | 1.5 oz. |
| Sesame Seed Oil | 1.5 oz. |
| Castor Oil | ½ |
| Argan Oil | ½ oz. |
| *Eclipta alba* | 1 tsp |
| Rosemary essential oil | 12 drops |
| Grapefruit essential oil | 14 drops |
| Peppermint essential oil | 20 drops |

The carrier oils, i.e. the sweet almond oil, sesame seed oil, castor oil, and argan oil, are added via a funnel into a container that can be capped. Next the *Eclipta alba* is added, followed by adding the rosemary, grapefruit, and peppermint essential oils by a dropper. The container is capped and shaken well to mix ingredients.

The composition can be packaged in an ordinary bottle or dispensing bottle.

The composition is useful for treating the scalp and hair and in particular for curl types 3B to 4C.

For use for scalp care, the product is massaged into scalp two to three times a week. Depending on hair type, the user can leave the product on. For example, users with non-curly hair types may prefer to leave the product on for half an hour or over night before washing out.

For moisturizing the hair, the product is evenly applied through the length of the hair. The product can also be applied to beards for added softness.

The product can be used as a base in combination with the curl lock creams of Examples 5 to 8, below.

The composition can provide cosmetic benefits to the scalp and hair and to enhance the appearance of the hair and its feel of thickness and to reduce frizz and split ends.

Example 4: Lock Length Oil Formula

The following composition is prepared using standard mixing equipment and procedures.

| Ingredient | Amount |
| --- | --- |
| Sweet Almond Oil | 1.5 oz. |
| Sesame Seed Oil | 1.5 oz. |
| Jamaican Black Castor Oil | ½ oz. |
| Argan Oil | ½ oz. |
| *Eclipta alba* | 1 tsp |
| Rosemary essential oil | 12 drops |
| Grapefruit essential oil | 14 drops |
| Peppermint essential oil | 20 drops |

The carrier oils, i.e. the sweet almond oil, sesame seed oil, Jamaican black castor oil, and argan oil are added via a funnel into a container that can be capped. Next the *Eclipta alba* is added, followed by adding the rosemary, grapefruit, and peppermint essential oils by a dropper. The container is capped and shaken well to mix ingredients.

The composition can be packaged in an ordinary bottle or dispensing bottle.

The composition is useful for treating the scalp and hair and in particular for curl types 3B to 4C.

For use for scalp care, the product is massaged into scalp two to three times a week. Depending on hair type, the user can leave the product on. For example, users with non-curly hair types may prefer to leave the product on for half an hour or over night before washing out.

For moisturizing the hair, the product is evenly applied through the length of the hair. The product can also be applied to beards for added softness.

The product can be used as a base in combination with the curl lock creams of Examples 5 to 8, below.

The composition can provide cosmetic benefits to the scalp and hair and to enhance the appearance of the hair and its feel of thickness and to reduce frizz and split ends.

Example 5: Curl Lock Cream Formula

The following composition is prepared using standard mixing equipment and procedures. Note that the amounts and percentages may in some instances be approximations of each other.

| Ingredient | Amount | Weight Percentage |
|---|---|---|
| Shea Butter | 115.44 grams | 16.92% |
| Sesame Seed Oil | 40.81 | 5.98 |
| Coconut Oil | 27.38 | 4.01 |
| Sweet Almond Oil | 27.21 | 3.99 |
| *Eclipta alba* | 9.07 | 1.33 |
| Cetearyl Alcohol | 16.03 | 2.35 |
| Vegetable Glycerin | 200.35 | 29.37 |
| Rosemary e.o. | 2.60 | 0.38 |
| Grapefruit e.o. | 3.44 | 0.50 |
| Vanilla e.o. | 1.68 | 0.25 |
| Pomegranate Oil | 0.27 | 0.04 |
| Coconut Water (room temperature) | 188.97* | 27.70 |
| Xanthan Gum | 2.24 | 0.33 |
| Arrowroot Powder | 46.74 | 6.85 |

*The coconut water can be Q.S. (quantum satis or quantum sufficit) which means as much as is sufficient or amount which is enough, e.g. to get to 100%, e.g. Q.S. 100%.

Using a double boiler or other non-direct heating source such as hot water bath, The shea butter, sesame seed oil, coconut oil, sweet almond oil, *Eclipta alba*, and cetearyl alcohol are combined with stirring and heating in a double boiler or other vessel and indirect heating source such as a water bath. Once the mixture is uniform and melted the xanthan gum is added with stirring until dissolved.

The resultant mixture is cooled in a refrigerator or freezer until a thick ring of hardened product forms. The cooling time can vary but is about 10 to 12 minutes in a 42 degree F. refrigerator. Upon visual inspection, a thin hardened layer generally forms over the middle of the mixture and the middle should appear darker than a lighter-colored ring that forms.

Next, the rosemary, grapefruit, vanilla, and pomegranate essential oils and the vegetable glycerin are added with vigorous mixing until homogeneous.

Next, the coconut water is added with vigorous mixing to form a thick emulsion. This step may take 7 to 10 minutes to reach the desired consistency.

To this resulting mixture the arrowroot powder is gradually added, first with gentle mixing to avoid causing a dust cloud of the powder and then with more vigorous mixing until creamy.

The composition can be packaged in a jar or tube.

The composition is useful for treating hair and in particular for curl types 2B to 4C.

For use, the composition is distributed evenly and in sections on wet hair from root to tip. The focus can be on the length of the hair to secure defined curls. In further embodiments the product can be paired with an oil product such as a lock length oil which is used as a base. See Examples 1 to 4, above.

The composition can help to lock in moisture and provide shine while enhancing the shape and bounce of curly locks. Although intended as a cosmetic product, the composition can provide benefits for the hair and scalp, and especially for frizz prone hair.

Example 6: Curl Lock Cream Formula

The following composition is prepared using standard mixing equipment and procedures. Note that the amounts and percentages may in some instances be approximations of each other.

| Ingredient | Amount | Weight Percentage |
|---|---|---|
| Shea Butter | 4 oz. | 16.51 |
| Sesame Seed Oil | 1.5 oz. | 6.19 |
| Coconut Oil | 1 oz. | 4.13 |
| Sweet Almond Oil | 1 oz. | 4.13 |
| *Eclipta alba* | 2 tsp | 1.37 |
| Cetearyl Alcohol | 1 oz. (2 tsp.) | 4.13 |
| Veg. Glycerin | 5 oz. | 20.64 |
| Rosemary e.o. | 2.5 droppers | 1.72 |
| Grapefruit e.o. | 3.5 droppers | 2.41 |
| Vanilla e.o. | 1.5 droppers | 1.03 |
| Pomegranate Oil | 4 drops | 0.17 |
| Coconut Water (room temperature) | 6 oz. | 24.76 |
| Xanthan Gum | ½ + ⅛ tsp. | 0.43 |
| Arrowroot Powder | 6 tbsp. | 12.38 |

Using a double boiler or other non-direct heating source such as hot water bath, The shea butter, sesame seed oil, coconut oil, sweet almond oil, *Eclipta alba*, and cetearyl alcohol are combined with stirring and heating in a double boiler or other vessel and indirect heating source such as a water bath. Once the mixture is uniform and melted the xanthan gum is added with stirring until dissolved.

The resultant mixture is cooled in a refrigerator or freezer until a thick ring of hardened product forms. The cooling time can vary but is about 10 to 12 minutes in a 42 degree F. refrigerator. Upon visual inspection, a thin hardened layer generally forms over the middle of the mixture and the middle should appear darker than a lighter-colored ring that forms.

Next, the rosemary, grapefruit, vanilla, and pomegranate essential oils and the vegetable glycerin are added with vigorous mixing until homogeneous.

Next, the coconut water is added with vigorous mixing to form a thick emulsion. This step may take 7 to 10 minutes to reach the desired consistency.

To this resulting mixture the arrowroot powder is gradually added, first with gentle mixing to avoid causing a dust cloud of the powder and then with more vigorous mixing until creamy.

The composition can be packaged in a jar or tube.

The composition is useful for treating hair and in particular for curl types 2B to 4C.

For use, the composition is distributed evenly and in sections on wet hair from root to tip. The focus can be on the length of the hair to secure defined curls. In further embodiments the product can be paired with an oil product such as a lock length oil which is used as a base. See Examples 1 to 4, above.

The composition can help to lock in moisture and provide shine while enhancing the shape and bounce of curly locks. Although intended as a cosmetic product, the composition can provide benefits for the hair and scalp, and especially for frizz prone hair.

Example 7: Curl Lock Cream Formula

The following composition is prepared using standard mixing equipment and procedures.

| Ingredient | Amount |
| --- | --- |
| Shea Butter | 5 oz. (8.5 tbsp.) |
| Sesame Seed Oil | 1.5 oz. |
| Coconut Oil | 1 oz. |
| Sweet Almond Oil | 1 oz. |
| *Eclipta alba* | 4 tsp. |
| Cetearyl Alcohol | 1 oz. (2 tsp.) |
| Veg. Glycerin | 5 oz. |
| Rosemary e.o. | 2.5 droppers |
| Grapefruit e.o. | 3.5 droppers |
| Vanilla e.o. | 3 droppers |
| Pomegranate Oil | 6 drops |
| Coconut Water (room temperature) | 7 oz. |
| Xanthan Gum | ½ + 18 tsp. |
| Arrowroot Powder | 8 tbsp. |

Using a double boiler or other non-direct heating source such as hot water bath, The shea butter, sesame seed oil, coconut oil, sweet almond oil, *Eclipta alba*, and cetearyl alcohol are combined with stirring and heating in a double boiler or other vessel and indirect heating source such as a water bath. Once the mixture is uniform and melted the xanthan gum is added with stirring until dissolved.

The resultant mixture is cooled in a refrigerator or freezer until a thick ring of hardened product forms. The cooling time can vary but is about 10 to 12 minutes in a 42 degree F. refrigerator. Upon visual inspection, a thin hardened layer generally forms over the middle of the mixture and the middle should appear darker than a lighter-colored ring that forms.

Next, the rosemary, grapefruit, vanilla, and pomegranate essential oils and the vegetable glycerin are added with vigorous mixing until homogeneous.

Next, the coconut water is added with vigorous mixing to form a thick emulsion. This step may take 7 to 10 minutes to reach the desired consistency.

To this resulting mixture the arrowroot powder is gradually added, first with gentle mixing to avoid causing a dust cloud of the powder and then with more vigorous mixing until creamy.

The composition can be packaged in a jar or tube.

The composition is useful for treating hair and in particular for curl types 2B to 4C.

For use, the composition is distributed evenly and in sections on wet hair from root to tip. The focus can be on the length of the hair to secure defined curls. In further embodiments the product can be paired with an oil product such as a lock length oil which is used as a base. See Examples 1 to 4, above.

The composition can help to lock in moisture and provide shine while enhancing the shape and bounce of curly locks. Although intended as a cosmetic product, the composition can provide benefits for the hair and scalp, and especially for frizz prone hair.

Example 8: Curl Lock Cream Formula

The following composition is prepared using standard mixing equipment and procedures.

| Ingredient | Amount |
| --- | --- |
| Mango Butter | 4 oz. |
| Sesame Seed Oil | 1.5 oz. |
| Coconut Oil | 1 oz. |
| Sweet Almond Oil | 1 oz. |
| *Eclipta alba* | 2 tsp |
| Glyceryl Stearate | 1 oz. |
| Veg. Glycerin | 5 oz. |
| Rosemary e.o. | 2.5 droppers |
| Grapefruit e.o. | 3.5 droppers |
| Vanilla e.o. | 1.5 droppers |
| Pomegranate Oil | 4 drops |
| Coconut Water (room temperature) | 6 oz. |
| Xanthan Gum | ½ + 18 tsp. |
| Arrowroot Powder | 6 tbsp. |

Using a double boiler or other non-direct heating source such as hot water bath, The mango butter, sesame seed oil, coconut oil, sweet almond oil, *Eclipta alba*, and glyceryl stearate are combined with stirring and heating in a double boiler or other vessel and indirect heating source such as a water bath. Once the mixture is uniform and melted the xanthan gum is added with stirring until dissolved.

The resultant mixture is cooled in a refrigerator or freezer until a thick ring of hardened product forms. The cooling time can vary but is about 10 to 12 minutes in a 42 degree F. refrigerator. Upon visual inspection, a thin hardened layer generally forms over the middle of the mixture and the middle should appear darker than a lighter-colored ring that forms.

Next, the rosemary, grapefruit, vanilla, and pomegranate essential oils and the vegetable glycerin are added with vigorous mixing until homogeneous.

Next, the coconut water is added with vigorous mixing to form a thick emulsion. This step may take 7 to 10 minutes to reach the desired consistency.

To this resulting mixture the arrowroot powder is gradually added, first with gentle mixing to avoid causing a dust cloud of the powder and then with more vigorous mixing until creamy.

The composition can be packaged in a jar or tube.

The composition is useful for treating hair and in particular for curl types 2B to 4C.

For use, the composition is distributed evenly and in sections on wet hair from root to tip. The focus can be on the length of the hair to secure defined curls. In further embodiments the product can be paired with an oil product such as a lock length oil, which is used as a base. See Examples 1 to 4, above.

The composition can help to lock in moisture and provide shine while enhancing the shape and bounce of curly locks. Although intended as a cosmetic product, the composition can provide benefits for the hair and scalp, and especially for frizz prone hair.

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and compositions of the present invention, where the term comprises is used with respect to the recited steps of the methods or components of the compositions, it is also contemplated that the methods and compositions consist essentially of, or consist of, the recited steps or components. Furthermore, the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Furthermore, it should be recognized that in certain instances a composition can be described as composed of the components prior to mixing, because upon mixing certain components can further react or be transformed into additional materials.

All percentages and ratios used herein, unless otherwise indicated, are by weight. It is recognized the mass of an object is often referred to as its weight in everyday usage and for most common scientific purposes, but that mass technically refers to the amount of matter of an object, whereas weight refers to the force experienced by an object due to gravity. Also, in common usage the "weight" (mass) of an object is what one determines when one "weighs" (masses) an object on a scale or balance.

What is claimed is:

1. A composition for treating hair consisting of *Eclipta alba*, sweet almond oil, sesame seed oil, argan oil, castor oil, rosemary essential oil, grapefruit essential oil, and peppermint essential oil.

2. The composition according to claim 1 wherein the *Eclipta alba* comprises from about 1% to about 5% by weight of the composition.

3. The composition according to claim 1 wherein the hair is human hair.

4. The composition according to claim 3 wherein the human hair is selected from wavy Type 2 human hair, curly Type 3 human hair, or coily/kinky Type 4 human hair.

5. A kit for treating human hair comprising the product of claim 1 and instructions for using.

6. The kit according to claim 5 further comprising a companion cream product for treating hair.

7. A method for treating human scalp hair comprising applying an effective amount of a composition according to claim 1 to human scalp hair.

8. A method for styling human scalp hair comprising applying an effective amount of a composition according to claim 1 to human scalp hair.

9. A method for conditioning human scalp hair comprising applying an effective amount of a composition according to claim 1 to human scalp hair.

10. A method for treating human beard hair comprising applying an effective amount of a composition according to claim 1 to human beard hair.

11. A method for treating or massaging the scalp of a human comprising applying or massaging an effective amount of a composition according to claim 1 to the scalp.

12. A method for making a composition for treating hair according to claim 1 comprising the step of combining *Eclipta alba*, sweet almond oil, sesame seed oil, argan oil, castor oil, rosemary essential oil, grapefruit essential oil, and peppermint essential oil.

* * * * *